United States Patent [19]

Hain et al.

[11] Patent Number: 5,589,626
[45] Date of Patent: *Dec. 31, 1996

[54] USE OF LYSOZYME GENE STRUCTURES IN PLANTS TO INCREASE RESISTANCE

[75] Inventors: Rüdiger Hain, Langenfeld; Klaus Stenzel, Duesseldorf, both of Germany

[73] Assignee: Bayer Aktiengesellschaft, Leverkusen, Germany

[ * ] Notice: The term of this patent shall not extend beyond the expiration date of Pat. No. 5,349,122.

[21] Appl. No.: 389,085

[22] Filed: Feb. 14, 1995

Related U.S. Application Data

[60] Continuation of Ser. No. 163,493, Dec. 7, 1993, abandoned, which is a division of Ser. No. 555,557, Jul. 19, 1990, Pat. No. 5,349,122.

[30] Foreign Application Priority Data

Aug. 10, 1989 [DE] Germany ........................... 39 26 390.8

[51] Int. Cl.⁶ ............................... A01H 5/00; A01H 5/10; C12N 15/56; C12N 15/82
[52] U.S. Cl. ......................... 800/205; 800/250; 800/255; 435/69.1; 435/69.7; 435/69.8; 435/70.1; 435/172.3; 435/206; 435/240.4; 435/240.47; 435/320.1; 536/23.2; 536/23.4; 536/23.5
[58] Field of Search ................... 435/69.1, 69.7, 435/69.8, 70.1, 172.3, 240.4, 240.47, 320.1, 206; 800/205, 250, 255; 536/23.2, 23.4, 23.5

[56] References Cited

U.S. PATENT DOCUMENTS 5,349,122  9/1994  Hain et al. .............................. 800/205

FOREIGN PATENT DOCUMENTS 8904371  5/1989  WIPO ............................. C12P 21/00

OTHER PUBLICATIONS

During, K. 1988, Ph.D. Thesis, Univ. of Koln, Germany, pp. 150–151, 156–157.
Velten et al. 1985. Nucleic Acids Res. 13(19): 6981–6998.
Rogers, J. 1985. J. Biol. Chem. 260(6):3731–3738.
van den Broeck et al. 1985. Nature 313: 358–363.

*Primary Examiner*—David T. Fox
*Attorney, Agent, or Firm*—Sprung Horn Kramer & Woods

[57] ABSTRACT

A method for increasing the resistance of a plant to fungi and animal pests comprising introducing into the genome of the plant one or more lysozyme gene structures which express lysozyme, the lysozyme gene structure comprises a chimeric gene fusion of the TR promoter, the signal peptide sequence of barley alpha-amylase and one or more lysozyme genes.

41 Claims, 1 Drawing Sheet

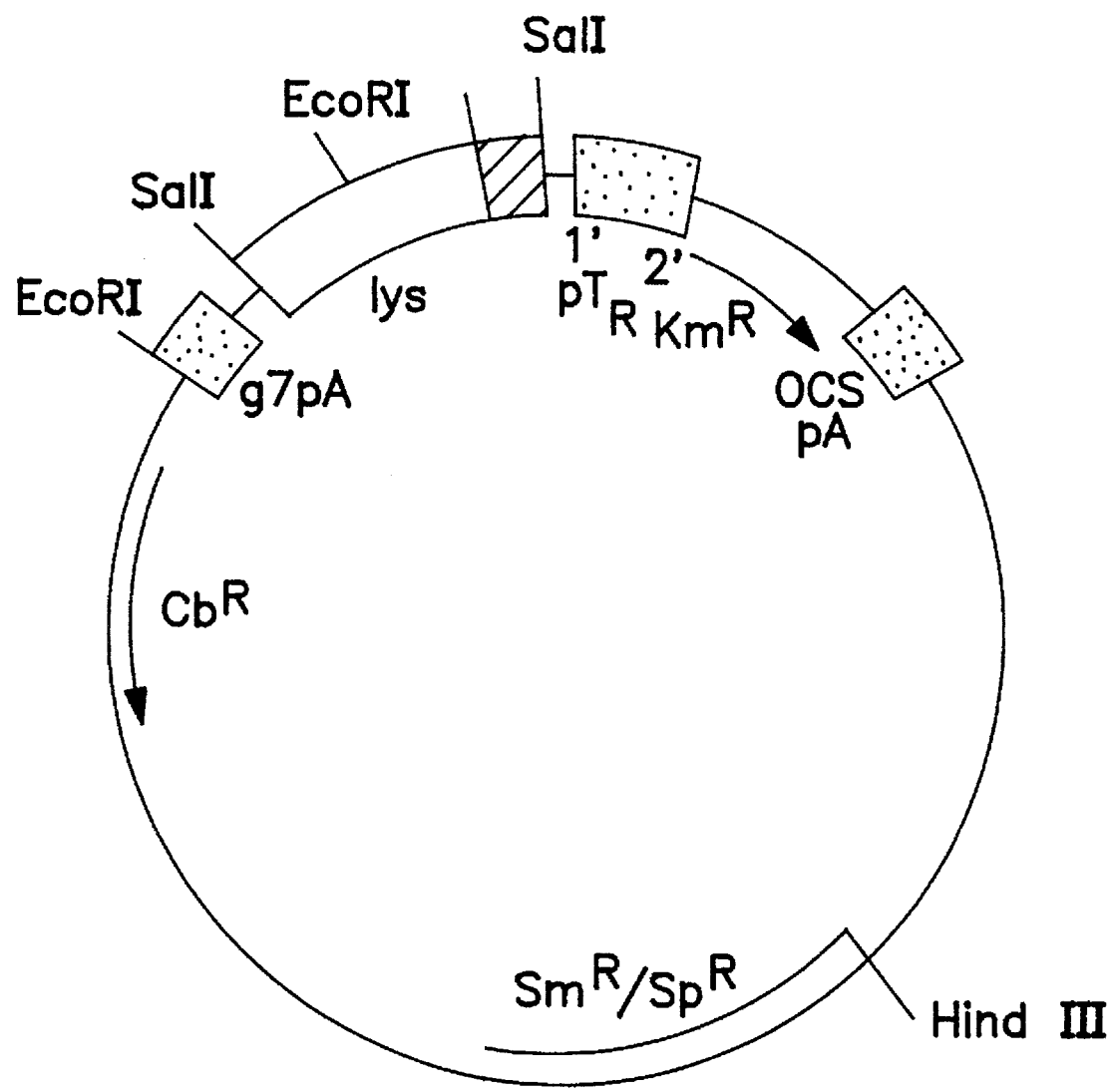

USE OF LYSOZYME GENE STRUCTURES IN PLANTS TO INCREASE RESISTANCE

This application is a continuation of application Ser. No. 08/163,493, filed Dec. 7, 1993, now abandoned; which is a divisional of application Ser. No. 07/555,557, filed Jul. 19, 1990, now U.S. Pat. No. 5,349,122, issued Sep. 20, 1994.

BACKGROUND OF THE INVENTION

The present invention relates to the use of lysozyme gene structures in plants for increasing the resistance of plants to fungi and animal pests.

A large proportion of the world's harvest of crop plants is constantly destroyed by pests (in 1967, the potential crop loss was 35%; cf. Chemistry of Pesticides, edited by K. H. Büchel, John Wiley & Sons, New York, 1983, page 6). There is therefore an urgent demand to research into, and utilize, all possible means which are suitable for reducing, or preventing, the infestation of crop plants with pests.

Patent application WO 89/04371 describes the transformation of plants having specific lysozyme genes for increasing the resistance to specific bacteria.

SUMMARY OF THE INVENTION

It has now been found that an increased resistance of plants to fungi and animal pests can be achieved by introducing into the genome of the plants one or more (preferably one) lysozyme gene structures, which express lysozymes and which are characterized in that they consist of chimetic gene fusions of the TR promoter, the signal peptide sequence of barley alpha-amylase and one or more (preferably one) lysozyme genes or contain these chimeric gene fusions.

With the knowledge of the prior art, it was surprising and could not have been predicted that a particularly pronounced resistance of plants to pathogens could be achieved with the aid of the gene structures which can be used according to the invention.

The term lysozymes describes a group of enzymes EC 3.2.1.17, which occur in nature. Examples which may be mentioned are chicken albumin lysozyme and T4-phage lysozyme.

Lysozyme genes are understood as meaning any nucleic acid (DNA) which, after having been transcribed into RNA and translated into protein, effects (in a suitable environment) the formation of an enzyme which has the known properties of lysozymes.

The lysozyme gene structures or their components can contain other DNA sequences, for example, at their beginning and/or end, which do not hinder their function, or not to a great extent.

The lysozyme genes and the other components of lysozyme gene structures can be present in the same form as they are contained in the genome of the organism from which they originate ("genomic" form, including non-lysozyme-encoding and/or non-regulatory sequences (such as introns), or in a form which corresponds to cDNA ("copy"DNA), which can be obtained via mRNA with the aid of reverse-transcriptase/polymerase (and no longer contains introns).

In the lysozyme gene structures which ca be used according to the invention, it is possible for DNA sequences to be replaced by other DNA sequences which act essentially in the same sense.

They can also have, at the ends, those DNA sequences which suit the particular manipulation of the genes (for example "linkers").

Preferred lysozyme gene structures which can be used according to the invention consist of, or contain, chimeric gene fusions which, in addition to the lysozyme gene(s), contain the TR promoter and the signal peptide sequence of barley alpha-amylase, as they occur in plasmid pSR 2–4.

Lysozyme gene structures which are preferred according to the invention contain the chicken albumin lysozyme gene and/or the T4-phage lysozyme gene. The T4-phase lysozyme gene is particularly preferred. The gene which is especially preferably used according to the invention is the T4-phage lysozyme gene as it occurs in plasmid pSR 2–4, as well as the DNA sequences which essentially act in the same sense.

The use of the chimeric gene fusion of the TR promoter, the signal peptide sequence of barley alpha-amylase and the protein-encoded region of the T4-phage lysozyme gene as contained in plasmid pSR 2–4, may be particularly emphasized.

If required, the sequence with the gene fusion which consists of the T4-phage lysozyme gene, the TR promoter and the signal peptide sequence of barley alpha-amylase or which contains this gene fusion, can be obtained by customary methods from plasmid pSR. 2–4 with the aid of restriction enzymes.

The lysozyme genes can be completely present in the gene structures, that is to say with their natural regulatory parts (in particular promoters) or only in the form of the structural genes which encode the protein lysozyme.

The *Escherichia coli* strain TBI pSR 2–4, which contains plasmid pSR 2–4, was deposited at the Deutsche Sammlung von Mikroogranismen [German Collection of Microorganisms] (DSM), Mascheroder Weg 1 b, D-3300 Braunschweig, Federal Republic of Germany, in compliance with the provision of the Budapest Convention on International Acknowledgment of the Deposition of Microorganisms for the Purpose of Patent Proceedings, and has the deposit number DSM 5455 (date of deposition: 25th Jul. 1989).

According to the invention it is possible to achieve resistance properties, or increased resistance properties, to pests, in particular fungi and animal pests, in particular arthropods, such as insects and mites, and also nematodes. Particularly emphasized in this context are the phytopathogenic fungi.

The harmful insects are in particular insects of the following orders:

Orthoptera, Dermaptera, Isoptera, Thysanoptera, Heteroptera, Homoptera, Lepidoptera, Coleoptera, Hymenoptera and Diptera.

The harmful mites are in particular: Tarsonemus spp., Panonychus spp. and Tetranychus spp.

The harmful nematodes are in particular:

Pratylenchus spp., Heterodera spp. and Meloidogyne spp.

The phytopathogenic fungi are in particular:

Plasmodiophoromycetes, Oomycetes, Chytridiomycetes, Zygomycetes, Ascomycetes, Basidigmycetes, Deuteromycetes.

Some pathogens causing fungal diseases which come under the generic names listed above may be mentioned as examples, but not by way of limitation:

Pythium species, such as, for example, *Pythium ultimum*;

Phytophthora species, such as, for example, *Phytophthora infestans*;

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Heminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria longipes* and

Pseudocercosporella species, such as, for example, *Pseudocercosporella herpotrichoides.*

Moreover, *Helminthosporium carbonum* may be mentioned.

According to the invention it is possible to impart virtually into all plants a resistance, or increased resistance, to the above pests. Naturally, there is a particular demand for the generation of resistance in the crop plants, such as forest plants, for example firs, spruces, douglasias, pines, larches, beeches and oaks, as well as in plants which produce foodstuffs and raw materials, for example cereals (in particular wheat, rye, barley, oats, millet, rice and corn), potatoes, pulses, soya beans, peanuts, vegetables (in particular cabbage species and tomatoes), fruit (in particular apples, pears, cherries, grapes, citrus, pineapple and bananas), oil palms, tea, cocoa and coffee bushes, tobacco, sisal and cotton, and in medicinal plants, such as Rauwolfia and Digitalis.

As already suggested, the lysozyme gene structures are introduced according to the invention in one or more copies (at the same locus or different loci of the genome) into the natural plant genome. In plants which are already capable of lysozyme synthesis, the introduction of one or more additional, optionally "foreign" lysozyme genes can result in a markedly increased resistance behavior.

As already mentioned, the increased resistance of the plant cells and plants transformed according to the present invention is important in agriculture and forestry, in the production of ornamental plants and medicinal plants, and in plant breeding. When plant cells are cultured, for example, for obtaining pharmaceutically useful substances, it is also advantageous to have plant cells available which have increased resistance properties, in particular to fungi.

The present invention therefore also relates to a method for preparing transformed plant cells (including protoplasts) and plants (including seeds and parts of plants) having an increased resistance to fungi and animal pests, which method is characterized in that (a) one or more lysozyme gene structures which consist of chimaeric gene fusions of the TR promoter, the signal peptide sequence of barley alpha-amylase and one or more lysozyme genes or contain these chimaeric gene fusions are introduced into the genome of plant cells (including protoplasts) and, if appropriate, (b) complete transformed plants are regenerated from the transformed plant cells (including protoplasts), and, if appropriate, (c) the desired parts of plants (including seeds) are obtained from the resulting transformed plants or their progeny.

Transformed plant cells (including protoplasts) and plants (including seeds and parts of plants) which have an increased resistance to fungi and animal pests and which contain one or more of the lysozyme gene structures, as well as those transformed plant cells and plants which can be obtained by the above method, are also a subject of the present invention.

Parts of the present invention are also the:

(a) use of lysozyme gene structures which consist of chimeric gene fusions of the TR promoter, the signal peptide sequence of barley alpha-amylase and one or more lysozyme genes or contain these chimeric gene fusions and the use of vectors and of transformed microorganisms according to the invention which contain the lysozyme gene structure, for transforming plant cells (including protoplasts) and plants (including seeds and parts of plants) with the result of an increased resistance to fungi and animal pests, as well as the (b) use of the transformed plant cells (including protoplasts) and plants (including seeds and parts of plants) according to the invention for producing propagation material and for generating novel plants and propagation material thereof, and, quite generally, the (c) use of the lysozyme gene structure for combating and controlling fungi and animal pests by increasing the particular resistance properties.

There is available a number of various methods for introducing the lysozyme gene structure into the genetic material of plants, or plant cells. The genes can be transferred by the generally customary known methods, and those skilled in the art can determine the method suitable for each case without difficulties.

The Ti-plasmid of *Agrobacterium tumefaciens* is available as a particularly favorable and widely usable vector for transferring foreign DNA into the genomes of dicotyledonous and monocotyledonous plants. The lysozyme gene structure is introduced into the T-DNA of suitable Ti plasmids (for example Zambryski et al. 1983) and is transferred by infecting the plant, infecting leaf discs or coculturing protoplasts with *Agrobacterium tumefaciens*.

Alternatively, lysozyme gene structure can be incubated together with plant protoplasts (for example, Davey et al. 1980; Hain et al., 1985; Krens et al., 1982; Paszkowski et al., 1984) in the presence of polycations or calcium salts and polyethylene glycol.

DNA uptake can also additionally be facilitated by an electrical field (electroporation) (for example Fromm et al. 1986).

The DNA can also be introduced in a known manner via plant pollen by "bombarding" pollen with physically accelerated particles carrying the DNA (cf. EP-A 0,270,356).

The plants are regenerated in a known manner with the aid of suitable culture media (for example, Nagy and Maliga 1976).

For example, the plasmid pSR 2–4 can be transferred to *Agrobacterium tumefaciens* containing, for example, pGV 3850, or derivatives thereof (Zambryski et al. 1983), with customary methods (for example, Van Haute et al. 1983). The success of the transformation can be checked by detecting nopalin or NPT(II). Alternatively, the lysozyme gene structure can be cloned in a binary vector (for example, Koncz and Schell 1986) and transferred as described above to a suitable Agrobacterium strain (Koncz and Schell 1986). The resulting Agrobacterium strain, which contains the lysozyme gene structure into a form which can be transferred into plants, is used further for transforming plants.

In a preferred embodiment, the isolated plasmid pSR 2–4 is transferred to plant protoplasts in a customary manner by direct gene transfer (for example, Hain et al 1985). In this method, the plasmid can be present in circular, but preferably in linear, form.

If plasmid pSR 2–4 is used with a reporter gene, kanamycin-resistant protoplasts are then tested for lysozyme expression.

Transformed (transgenic) plants, or plant cells, are prepared by known methods, for example by leaf-disc transformation (for example Horsch et al. 1985), by coculturing regenerating plant protoplasts or cell cultures with *Agrobacterium tumefaciens* (for example Marton et al. 1979, Hain et al. 1985), or by direct DNA-transfection. Resulting transformed plants are detected either by selection for reporter gene expression, for example, by phosphorylation of kanamycin sulphate in vitro (Reis et al. 1984; Schreier et al. 1985), or by the expression of nopalin synthase (according to Aerts et al. 1983) or of lysozyme by Northern-blot analysis and Western blot analysis. It is also possible to detect the lysozyme in transformed plants in a known manner using specific antibodies.

The transformed plant cells are cultured and regenerated to complete plants by the generally customary methods with the aid of the specifically suitable culture media.

The transformed plant cell as well as the transformed plants which contain lysozymes, show a considerably better resistance to phytopathogenic fungi and animal pests, in particular to insects, mites and nematodes.

The term "plants" in connection with the present invention denotes complete plants but also parts of plants, such as leaves, seeds, tubers, cuttings etc. "Plant cells" include protoplasts, cell lines, plant calli etc. "Propagation material" denotes plants and plant cells which can be used for multiplying the transformed plants and plant cells.

The term "DNA sequences which essentially act in the same sense" in the present connection means that the invention also comprises those modifications in which the function of the lysozyme genes, or parts thereof, is not affected to an extent that lysozyme is no longer formed, or that the regulatory gene part is no longer effective. The appropriate modifications can be effected by replacing, adding and/or removing DNA sequences, individual codons and/or individual nucleic acids.

"Mutants" in the microorganisms which can be used according to the invention denotes those modified microorganisms which still have the features which are essential for carrying out the invention, in particular the specific plasmids.

BRIEF DESCRIPTION OF THE FIGURE

FIG. 1 shows plasmid pSR 2–4.

DETAILED DESCRIPTION OF THE PREFERRED EMBODIMENTS

The following exemplary embodiments are intended to illustrate the present invention in greater detail:
1. Description of the plasmid construction pSR 2–4 used (cf. FIG. 1)

Plasmid pSR 2–4 contains a chimeric gene fusion which has been constructed in the expression vector pAP 2034 (Velten and Schell 1985) from the TR promoter (Velten et al. 1984), the signal peptide sequence of barley alpha-amylase and the protein-encoding region of the T4-phage lysozyme gene (K. During, Dissertation, Cologne University 1988).

The plasmid pSR 2–4 has the size of 9.3 kb. FIG. 1:
Plasmid pSR2–4 (9.3 kb) can be illustrated as follows:

$pT_R$=dual plant promoter from *A. tumefaciens* ocs pA=polyadenylation sequence region of octopin synthase $Km^R$=kanamycin resistance gene, active in plants g7pA=polyadenylation region of Agrobacterium gene 7

$Cb^R$=Carbpenicillin resistance gene $Sm^R$=Streptomycin resistance gene $Sp^R$=Spectomycin resistance gene Hatched region=signal peptide sequence of barley alpha-amylase lys=encoding sequence for T4-phage lysozyme The lysozyme gene structure was transferred following the methods described below, for example, into tobacco and potatoes.

As already explained above, *E. coli* strain TBI pSR 2–4, which contains the plasmid pSR 2–4 in a form which can easily be isolated, has been deposited at the Deutsche Sammlung yon Mikroorganismen (German Collection of Microorganisms).
2. Transformation of tobacco
   a) Tobacco shoot culture and isolation of tobacco protoplasts:

*Nicotiana tabacum* (Petit Havanna SR1) is multiplied as a sterile shoot culture on hormone-free LS medium (Linsmaier and Skoog 1965).

Shoot cultures are transferred to fresh LS medium in intervals of about 6–8 weeks. The shoot cultures are kept in a growth cabinet at 12 hours light (1,000–3,000 lux) at 24°–26° C.

To isolate leaf protoplasts, about 2 g leaves (about 3–5 cm in length) are cut into small pieces (0.5 cm×1 cm), using a new razor blade. The leaf material is incubated in 20 ml of enzyme solution consisting of K3 medium (Nagy and Maliga 1976), 0.4 m sucrose, pH 5.6, 2% of Zellulase R10 (by Serva) and 0.5% of Macerozym R10 (by Serva) for 14–16 hours at room temperature. After this, the protoplasts are separated from cell debris by filtration over 0.30 mm and 0.1 mm steel sieves. The filtrate is centrifuged at 100×g for 10 minutes. During this centrifugation, intact protoplasts float and are collected in a band on the upper edge of the enzyme solution. The pellet of cell debris and the enzyme solution are removed by suction with a glass capillary. The precleaned protoplasts are made up to 10 ml with fresh K3 medium (0.4M sucrose as osmotically active agent) and re-floated. The wash medium is removed and the protoplasts are diluted to 1–2×10$^5$/ml for culturing or for subsequent infection with Agrobacteria (coculture). The protoplast concentration is determined in a hematocytometer.

b) Transformation of regenerating tobacco protoplasts by coculture with *Agrobacterium tumefaciens*:

In the following, the slightly modified method of Marton et al. 1979 is used. The protoplasts are isolated as described and incubated for 2 days in the dark and for one to two days under weak light (500 lux) at 26° C., at a density of 1–2×10$^5$/ml in K3 medium (0.4M sucrose, 0.1 mg/l NAA, 0.2 mg of kinetin). As soon as the first protoplast divisions take place, 30 µl of an Agrobacterium suspension in minimum A (Am) medium (density about 10$^9$ Agrobacteria/ml) are added to 3 ml regenerating protoplasts. The duration of the coculture is 3–4 days at 20° C., in the dark. After this, the tobacco cells are transferred into 12 ml centrifuge tubes, diluted with sea water (600 mOsm/kg) to 10 ml, and pelleted for 10 minutes at 60×g. This washing process is repeated 1 or 2 more times to remove most of the Agrobacteria. The cell suspension is cultured in K3 medium (0.3 m sucrose) with 1 mg/l NAA (naphthyl-1-acetic acid), 0.2 mg/l kinetin and 500 mg/l of the cephalosporin antibiotic cefotaxime, at a density of 5×10$^4$/ml. Each week, the cell suspension is diluted with fresh K3 medium, and the osmotic value of the medium is gradually reduced by 0.05 m sucrose (about 60 mOsm/kg) per week. 2 to 3 weeks after the coculture, the selection with kanamycin (100 mg/l kanamycin sulphate (by Sigma), 660 mg/g active kanamycin) is started in agarose-bead-type culture (Shillito et al. 1983). Kanamycin-resistant colonies can be distinguished 3–4 weeks after the beginning of the selection from the background of retarded colonies.

c) Direct transformation of tobacco protoplasts with DNA, calcium nitrate/PEG transformation About 10$^6$ protoplasts in 180 µl of K3 medium are carefully mixed in a Petri dish with 20 µl of aqueous DNA solution containing 0.5 µg of pSR 2–4 per µl. 200 µl of fusion solution (0.1M calcium nitrate, 0.45M mannitol and 25% of polyethylene glycol (PEG 6000), pH 9) are subsequently added carefully. After 15 minutes, 5 ml of wash solution (0.275M calcium nitrate, pH 6) are added, and, after a further 5 minutes, the protoplasts are transferred to a centrifuge tube and pelleted at 60×g. The pellet is taken up in a small amount of K3% medium and cultured as described in the next section. Alternatively, the protoplasts can be transformed as by Hain et al. 1985.

d) Culture of the protoplasts incubated with DNA, and selection of kanamycin-resistant calli A modified "bead-type culture" technique (Shillito et al. 1983) is used for the culture and selection of kanamycin-resistant colonies as described below. One week after the protoplasts have been treated with DNA (cf. c)), 3 ml of the cell suspension are mixed in 5 cm Petri dishes with 3 ml of K3% medium (0.3M sucrose+hormones; 1.2% (Seaplaque) LMT Agarose (low-melting agarose, by Marine Colloids). For this purpose, dry agarose is autoclaved, K3% medium is added, and the mixture is briefly boiled up i a microwave. After the agarose has solidified, the agarose discs (beads) together with the embedded tobacco microcalli are transferred to 10 cm Petri dishes for further culture and selection, and 10 ml of K3% medium (0.3M sucrose, 1 mg/l NAA, 0.2 mg/l kinetin) 100 mg/l of kanamycin sulphate (by Sigma) are added in each case. The liquid medium is changed every week. During this procedure, the osmotic value of the medium is lowered stepwise. The replacement medium (K3+Km) is reduced every week by 0.05M of sucrose ( about 60 mOsm ).

Selection diagram of kanamycin-resistant tobacco colonies after DNA transformation:

| 0.4M A E S | 0.3M | 0.25M | 0.20M | 0.15M K | 0.10M | Sucrose in the liquid medium |
|---|---|---|---|---|---|---|
| 1 | 2 | 3 | 4 | 5 | 6 | weeks after DNA uptake |

(K3 medium: 1 mg of NAA, 0.2 mg of kinetin)
A = DNA uptake
E = embedding in agarose
S = selection with kanamycin (100 mg/l kanamycin sulphate)
K = kanamycin-resistant colonies can unequivocally be distinguished from the background e) Regeneration of kanamycin-resistant plants As soon as the kanamycin-resistant colonies have reached a diameter of about 0.5 cm, one half of them is transferred to regeneration medium (LS medium, 2% of sucrose, 0.5 mg/l benzylaminopurine BAP) and kept in a growth chamber at 12 hours light (3,000–5,000 lux) and 24° C. The other half is propagated as callus culture on LS medium with 1 mg/l NAA, 0.2 mg/l kinetin, 0.1 mg/l BAP and 100 mg/l kanamycin sulphate. When the regenerated shoots have a size of about 1 cm, they are excised and transferred to ½ LS medium (1% of sucrose, 0.8% of agar) without growth regulators, for rooting. The shoots are rooted on ½ MS medium with 100 mg/l kanamycin sulphate and later transferred to soil.

f) Transformation of leaf discs by *Agrobacterium tumefaciens*

For the transformation of leaf discs (Horsch et al. 1985) leaves, about 2–3 cm in length, of sterile shoot cultures are punched into discs of diameter 1 cm, and the discs are incubated for about 5 minutes with a suspension of appropriate Agrobacteria (about 10$^9$/ml) (cf. b)) in Am medium, see below). The infected leaf segments are kept for 3–4 days at about 24° C. on MS medium (see below) without hormones.

During this time, Agrobacterium grows over the leaf segments. The leaf segments are subsequently washed in MS medium (0.5 mg/ml BAP, 0.1 mg/ml NAA), and placed on the same medium (0.8% of agar) with 500 µg/ml cefotaxime (Claforan) and 100 µg/ml of kanamycin sulphate (by Sigma). The medium should be renewed after two weeks. Transformed shoots become visible after a further 2–3 weeks. The regeneration of shoots should also be carried out parallel without selection pressure. The regenerated shoots must then be tested for transformation by biological tests, for example, for nopaline synthase or stilbene synthase activity. In this manner, 1–10% of transformed shoots are obtained.

Biochemical detection method of the transformation

Detection of nopaline in plant tissues:

Nopaline is detected as described by Otten and Schilperoort (1978) and Aerts et al. (1979), as follows. 50 mg of plant material (callus or leaf segments) are incubated overnight in an Eppendorf tube in LS medium with 0.1M arginine, at room temperature. The plant material is then blotted with adsorptive paper, homogenized in a new Eppendorf centrifuge tube using a glass rod, and the homogenizate is centrifuge for 2 minutes in an Eppendorf centrifuge. 2 µl of the supernatant are applied as dots on a paper suitable for electrophoresis (Whatman 3MM paper) (20×40 cm) and dried. The paper is saturated with the mobile phase (5% of formic acid, 15% of acetic acid, 80% of $H_2O$, pH 1.8) and electrophoresis is carried out for 45 minutes at 400 V. Nopaline moves towards the cathode. The paper is then dried in a hot stream of air and passed through phenanthrenequinone stain in the direction of the movement (equal volumes of 0.02% phenanthrenequinone in ethanol and 10% of NaOH in 60% strength ethanol). The dried paper is viewed under long-wave UV light and photographs are taken. With the reagent, arginine and arginine derivatives are stained fluorescent yellow.

Neomycin phosphotransferase (NPT II) enzyme assay:

NPT II activity in plant tissue is detected by in-situ phosphorylation of kanamycin as described by Reiss et al. (1984) and modified by Schreier et al. (1985). 50 mg of plant tissue are homogenized on ice in 50 µl of extraction buffer (10% glycerol, 5% 2-mercaptoethanol, 0.1% SDS, 0.025% Bromophenol Blue, 62.5 mM Tris pH 6.8) with the addition of glass powder, and the mixture is centrifuged in an Eppendorf centrifuge for 10 minutes a 4° C. 50 µl of the supernatant are transferred to a native polyacrylamide gel (145×110×1.2 mm; separation gel: 10% acrylamide, 0.33% bisacrylamide, 0.375M Tris pH 8.8, collecting gel: 5% acrylamide, 0.165% bisacrylamide, 0.125M Tris pH 6.8), and electrophoresis is effected overnight at 4° C. and 60 V. As soon as the Bromophenol Blue marker moves out of the gel, the gel is washed twice with distilled water for 10 minutes and once with reaction buffer for 30 minutes (67 mM Tris maleate, pH 7.1, 42 mM $MgCl_2$, 400 mM ammonium chloride). The gel is placed on a glass plate of the same size and covered with a layer of 40 ml of 1% strength agarose in reaction buffer containing the substrates kanamycin sulphate (20 µg/ml) and 20–200 uCi $^{32}P$ ATP (Amersham). The sandwich gel is incubated for 30 minutes at room temperature, and a sheet of phosphocellulose paper P81 (Whatman) is then placed on the agarose. On top of this there are arranged four layers of filter paper 3MM (Whatman) and a few paper towels. After 3–4 hours, the transfer of in-situ phosphorylated, radioactive kanamycin phosphate to the P81 paper is stopped. The P81 paper is incubated for 30 minutes in a solution of proteinase K and 1% sodium dodecyl sulphate (SDS) at 60° C. and then washed 3–4 times in 250 ml of 10 mM phosphate buffer pH 7.5 at 80° C., dried and autoradiographed for 1–12 hours at −70° C. (XAR5 film, Kodak).

Detection of T4-phage lysozyme gene expression a) Isolation of m-RNA from cell cultures and plants:

To isolate RNA from cell cultures and plants, 0.1 g of sterile quartz sand, 1 µl of β-mercaptoethanol and 1 ml of HO buffer (0.4M Tris/HCl pH 8, 0.1M NaCl, 0.04M EDTA, 5% SDS, 65° C. were added per gram of plant material and the mixture was homogenized. 1 ml of phenol/chloroform (1:1) was added, and the mixture was homogenized for about another 2 minutes. The homogenate was transferred to a centrifuge tube and the tube was shaken vigorously. After centrifugation (10', 10,000×g, room temperature), another 2 ml of phenol/chloroform were added, and the tube was shaken intensively and recentrifuged. To remove polysaccharides, ¼ of the volume of ethanol was added to the aqueous phase, the mixture was placed on ice for 10 minutes and then centrifuged for 10 minutes at 10,000×g and 4° C. The nucleic acid was subsequently precipitated with twice the volume of ethanol and stored at −70° C. The precipitated RNA was subsequently washed 2–3 times with 2 ml portions of sodium acetate (3M, pH 6). The RNA was dissolved in 100 µl sterile water.

b) Electrophoresis of RNA:

RNA denaturation for the e ectrophoresis of RNA, 3 µl of 5-fold buffer (0.2M MOPS, 50 mM sodium acetate, 5 mM EDTA pH 7), 5.25 µl of formaldehyde (37% strength) and 15 µl formamide (deionized) were added to 6.75 µl of RNA (20 µg) and denaturation was effected for 15 minutes at 56° C.

Preparation of agarose gels: 3.5 g of agarose were boiled up in 200 ml of water, the mixture was cooled to 60° C., and 70 ml of 5-fold buffer and 62 ml of formaldehyde were then added. The solution was made up with water to a volume of 350 ml and filled into the gel apparatus. The denaturated RNA was mixed with 3 µl color marker and 1 µl of ethidium bromide (5 mg/ml), and electrophoresis was effected for 6 hours at 100 V.

c) Northern blotting:

The gel was subsequently washed 3 times for 10 minutes in sterile water. The RNA was transferred to nitrocellulose filter (Maniatis et al. 1982) using a standard blotting procedure (3–4 hours in 20×SSC).

d) Hybridization on Northern blots:

100 ng of isolated Sal I fragment from pSR 2–4 were subjected to Nick-translation for radioactive labelling (specific activity >$4×10^8$ cpm/µg). Hybridization was carried out at 42° C. overnight, as described by Thomzik and Hain 1988.

This procedure was used for detecting the synthesis of T 4-phage-hysozyme-specific mRNA in transformed tobacco.

Detection of T4-phage lysozyme in tobacco by Western blotting

To isolate total protein from tobacco, 100 mg of plant material were homogenized in double-concentrated SDS sample buffer (150 mM Tris/HCl pH 6.8, 2% SDS, 20% glycerol, 0.004% Bromophenol Blue, 200 mM DTT, 5 mM ascorbic acid and 10 mM CHAPS) and the mixture was incubated for 5 minutes at 95° C. After centrifugation (10,000×g , 5 minutes), an aliquot of the supernatant (10–100 µg total protein) was transferred to 15% SDS polyacrylamide gel and electrophoresis was effected for 12 hours at 60 V. The separated proteins were then transferred by electroblotting (2 hours, 0.8–1 A) in transfer buffer (25 mM Tris base, 192 mM glycine and 20% methanol) to PVDF Immobilon membranes. The membrane was subsequently incubated for 30 minutes in 5% bovine serum albumen (BSA) in PBA. After three washes with 0.1% BSA in PBA, the membrane was incubated for 2 hours with a polyclonal T4-lysozyme-specific antibody. After three washes (5 minutes each) in 0.1% BSA/PBA, the membrane was incubated with a gold-labelled antibody (goat anti-rabbit, from Auro Probe$^R$ Kit, Janssen Chemie) for 2 hours as described by the manufacturer. After washes with 0.1% BSA in PBA and with water, the membrane was stained with enhancer/initiator (1:1).

3. Transformation of *Solanum tuberosum* potato

The transformation was transformed exactly in the manner described in EP-A 0,242,246, pages 14 to 15, the Agrobacteria containing Ti plasmids which carry the lysozyme gene structure of plasmid pSR 2–4.

All percentages in the above examples relate to per cent by weight, unless otherwise stated.

In the plant cells and plants obtained according to the above examples, the presence of the lysozyme gene was confirmed by Southern blot analysis. The expression of the lysozyme gene was detected by Northern blot analysis and lysozyme with the aid of specific antibodies. Transformed and non-transformed plants (for comparison) were sprayed with a spore suspension of *Botrytis cinera* and *Alternaria longipes*, and infestation with the fungus was scored 1 week later. Compared with the non-transformed comparison plants, the transformed plants showed an increased resistance to infestation with fungus.

Example of the detection of increased resistance

To test increased resistance to fungal plant diseases, by the lysozyme synthesized in the plants, the plants were inoculated with pathogens and the degree infestation was used as parameter.

The test pathogens used were *Alternaria longipes* (Ell. & Everh.) Mason and *Botrytis cinerea* Pers.

The tobacco plants are potted in pots (diameter 11 cm) containing standard soil (by Balster) and grown in the greenhouse at 23° C. and 70 to 80% relative humidity until the experiments are started. The plants are watered and fed as required. For inoculation, the leaves of the 5 to 8 weeks old plants are sprayed with spore suspensions oft he pathogens until running off. The plants are subsequently incubated under conditions favourable for the pathogens, at an initial relative humidity of 100% and at 21° C. After 4 to 8 days, the health state of the plants is determined in per cent on the basis of the infested leaf area.

As can be seen from the tables (I and II), plants transformed with pSR 2–4, according to Example 2, show a lower infestation with *Alternaria longipes* as well as with *Botrytis cinerea* than those of the wild type $SR_1$.

TABLE I

Effect of the lysozyme gene on the infestation of the tobacco plants with Alternaria longipes

| Plant | % infested leaf area on leaf | | | | | Reduction* |
|---|---|---|---|---|---|---|
| | 1 | 2 | 3 | 4 | x | |
| $SR_1$ wild type | 40 | 43 | 35 | 33 | 38 | — |
| Transformed plant | 14 | 11 | 2 | 2 | 7 | 82% |

*)Reduction calculated with Abbott's formula

TABLE II

Effect of the lysozyme gene on the infestation of the tobacco plants with Botrytis cinerea

| Plant | % infested leaf area on leaf | | | | | Reduction |
|---|---|---|---|---|---|---|
| | 1 | 2 | 3 | 4 | x | |
| $SR_1$ wild type | 100 | 100 | 100 | 100 | 100 | — |
| Transformed plant | 23 | 35 | 23 | 30 | 28 | 72% |

*)Reduction calculated by Abbott's formula

Some of the media employed in the transformation of plants or plant cells are described below:

Am medium

| | |
|---|---|
| 3.5 g | $K_2HPO_4$ |
| 1.5 g | $KH_2PO_4$ |
| 0.5 g | $Na_3$ citrate |
| 0.1 g | $MgSO_4 \times 7H_2O$ |
| 1 g | $(NH_4)_2SO_4$ |
| 2 g | glucose to 1 liter |

Medium for sterile shoot culture of tobacco

Macro-elements: ½ of the concentration of the MS salts
Micro-elements: ½ of the concentration of the MS salts

| Fe EDTA | Murashige and Skoog (MS) | |
|---|---|---|
| Myo-Inositol | | 100 mg/l |
| Sucrose | | 10 mg/l |
| Agar | | 8 g/l |
| Vitamins | Ca panthotenate | 1 mg/l |
| | Biotin | 10 mg/l |
| | Nicotinic acid | 1 mg/l |
| | Pyridoxine | 1 mg/l |
| | Thiamine | 1 mg/l |
| pH 5.7 before autoclaving | | |

K3 medium

For culturing *Nicotiana tabacum* petit Havana SR1, *Nicotiana tabacum* Wisconsin 38 and *Nicotiana plumaginifolia* protoplasts (Nagy and Maliga, 1976)

| Macro-elements | $NH_4NO_3$ | 250 mg/l |
|---|---|---|
| | $KNO_3$ | 2500 mg/l |
| | $CaCl_2 \times 2H_2O$ | 900 mg/l |
| | $MgSO_4 \times 7H_2O$ | 250 mg/l |
| | $NaH_2PO_4 \times 1H_2O$ | 150 mg/l |
| | $(NH_4)_2SO_4$ | 134 mg/l |
| | $CaHPO_4 \times 1H_2O$ | 50 mg/l |
| Micro-elements | $H_3BNO_3$ | 3 mg/l |
| | $MnSO_4 \times 1H_2O$ | 10 mg/l |
| | $ZnSO_4 \times 4H_2O$ | 2 mg/l |
| | KI | 0.75 mg/l |
| | $Na_2MoO_4 \times 2H_2O$ | 0.25 mg/l |
| | $CuSO_4 \times 5H_2O$ | 0.025 mg/l |
| | $CoCl_2 \times 6H_2O$ | 0.025 mg/l |
| Fe EDTA | $Na_2EDTA$ | 37.2 mg/l |
| | $FeSO_2 \times 7H_2O$ | 27.8 mg/l |
| Inositol | | 100 mg/l |
| Sucrose | | 137 g/l |
| | | (= 0.4M) |
| Xylose | | 250 mg/l |
| Vitamins | nicotinic acid | 1 mg/l |
| | pyridoxine | 1 mg/l |
| | thiamine | 10 mg/l |
| Hormone | NAA | 1.0 mg/l |
| | kinetin | 0.2 mg/l |
| pH 5.6 Filter sterilization | | |

Linsmaier and Skoog medium (Linsmaier and Skoog 1965)

For culturing regenerating protoplasts and for tissue culture of tobacco tumors and callus. Linsmaier and Skoog (LS) medium is Murashige and Skoog medium (Murashige and Skoog, 1962) with the following modifications:

thiamine weighed in a higher concentration 0.4 mg/l instead of 0.1 mg/l;

glycine, pyridoxine and nicotinic acid are absent.

| Macro-elements | NH$_4$NO$_3$ | 1650 mg/l |
| --- | --- | --- |
| | KNO$_3$ | 1900 mg/l |
| | CaCl$_2$ × 2H$_2$O | 440 mg/l |
| | MgSO$_4$ × 7H$_2$O | 370 mg/l |
| | KH$_2$PO$_4$ | 170 mg/l |
| Micro-elements | H$_3$BO$_3$ | 6.2 mg/l |
| | MnSO$_4$ × 1H$_2$O | 22.3 mg/l |
| | ZNSO$_4$ × 4H$_2$O | 8.6 mg/l |
| | KI | 0.83 mg/l |
| | Na$_2$MoO$_4$ × 2H$_2$O | 0.25 mg/l |
| | CuSO$_4$ × 5H$_2$O | 0.025 mg/l |
| | CoCl$_2$ × 6H$_2$O | 0.025 mg/l |
| Fe EDTA | Na$_2$EDTA | 37.2 mg/l |
| | FeSO$_4$ × 7H$_2$O | 27.8 mg/l |
| Inositol | | 100 mg/l |
| Sucrose | | 30 g/l |
| Agar | | 8 g/l |
| Vitamins | thiamine | 0.4 mg/l |
| Hormone | NAA | 1 mg/l |
| | kinetin | 0.2 mg/l |
| pH 5.7 before autoclaving | | |

The following literature references can be cited in connection with the transformation of plants or plant cells and with lysozyme genes which can be used according to the invention:

Aerts M., Jacobs M., Hernalsteens J. P., Van Montagu M., Schell J. (1983) Induction and in vitro culture of *Arabidopsis thaliana* crown gall tumours. Plant Sci. Lett. 17: 43–50;

Davey M. R., Cocking E. C., Freeman J., Pearce N., Tudor I. (1980) Transformation of Petunia protoplasts by isolated Agrobacterium plasmid. Plant Sci. Lett. 18: 307–313;

K. Düring, Dissertation, Cologne University, 1988: Wundinduzierbare Expression und Sekretion von T4 Lysozym und monoklonalen Antikörpern in *Nicotiana tabacum* [Woundinducible expression and secretion of T4-lysozyme and monoclonal antibodies in *Nicotiana tabacum*];

Fromm M. E., Taylor L. P., Walbot V. (1986) Stable transformation of maize after gene transfer by electroporation. Nature 319: 791–793;

Hain, R., Stabel, P., Czernilofsky, A. Pp., Steinbiss, H. H., Herrera-Estrella, L., Schell, J. (1985) Uptake, integration, expression and genetic transmission of a selectable chimeric gene by plant protoplasts, Molec. Gen. Genet. 199: 161–168;

Horsch R. B., Fry J. E., Hoffmann N. L., Eichholtz D., Rogers S. G., Fraley R. T. (1985) A simple and general method for transferring genes into plants. Science 277: 1229–1231;

Krens F. H., Molendijk L., Wullems G. J., Schilperoort R. A. (1982) in vitro transformation of plant protoplasts with Ti-plasmid DNA. Nature 296: 72–74;

Koncz C., Schell J. (1986) The promoter of T$_L$-DNA gene 5 controls the tissue-specific expression of chimaeric genes carried by a noval type of Agrobacterium linary vector. Mol. Gen. Genet. (1986) 204: 338–396;

Linsmaier D. M., Skoog F. (1965) Organic growth factor requirements of tobacco tissue cultures. Physiol Plant 18: 100–127;

Marton L., Wullems G. J., Molendijk L., Schilperoort P. R. (1979) In vitro transformation of cultured cells from *Nicotiana tabacum* by *Agrobacterium tumefaciens*. Nature 277: 1229–131.

Nagy J. I., Maliga P. (1976) Callus induction and plant regeneration from mesophyll protoplasts of *Nicotiana sylvestris*. Z. Pflanzenphysiol 78: 453–455;

Otten L. A. B. M., Schilperoort R. A. (1978) A rapid microscale method for the detection of Lyposin and Nopaline dehydrogenase activities. Biochim biophys acta 527: 497–500;

Paszkowski J., Shillito R. D., Saul M., Mandak V., Hohn T., Hohn B., Potrykus I. (1984) Direct gene transfer to plants. EMBO J. 3: 2717–2722;

Shillito R. D., Paszkowski J. Potrykus I. (1983) Agarose plating and Bead type culture technique enable and stimulate development of protoplast-derived colonies in an number of plant species. Pl Cell Rep 2: 244–247;

Maniatis T., Fritsch E. F., Sambrook J. eds. (1982) Molecular cloning, a laboratory manual. Cold Spring Harbor, N.Y.

J. E. Thomzik and R. Hain (1988), Transfer and segregation of triazine tolerant chloroplasts in Brassica napus L. Theor. Appl. Genet. (1988) 76: 165–171;

Van Haute E., Joos H., Maes M., Worren G., van Montagu M., Schell J. (1983) Inter generic transfer and exchange recombination of restriction fragments cloned in pBR 322: a novel strategy for the reversed genetics of the ti-plasmids of *Agrobakterium tumefaciens*. EMBO J. 2: 411–417; Velten J., Velten L., Hain R., Schell J. (1984) Isolation of a dual plant promotor fragment from the Ti Plasmid of *Agrobacterium tumefaciens*. EMBO J 12: 2723–2730;

Velten J., Schell J. (1985) Selection-expression plasmid vectors for the use in genetic transormation of higher plants. NAR 13: 6981–6998;

Zambryski P. Joos H., Genetello C., van Montagu M., Schell J. (1983) Ti-plasmid vector for the introduction of DNA into plant cells without altering their normal regeneration capacity, EMBO J. 12: 2143–2150;

Bernd Reiss, Rolf Sprengel, Hans Will and Heinz Schaller (1984) A new sensitive method for qualitative and quantitative assay of neomycin phosphotransferase in crude cell tracts, GENE 1081: 211–217;

Peter H. Schreier, Elisabeth A. Seftor, Jozef Schell and Hans J. Bohnert (1985) The use of nuclear-encoded sequences to direct the light-regulated synthesis and transport of a foreign protein into plant chloroplasts, EMBO J. Vol. 4, No. 1: 25–32.

The following published patent applications can also be listed:

EP-A 116,718
EP-A 159,418
EP-A 120,515
EP-A-120,516
EP-A-172,112
EP-A-140,556
EP-A-174,166
EP-A-122,791
EP-A-126,546
EP-A-164,597
EP-A-175,966
WO 84/02913
WO 84/02919
WO 84/02920
WO 83/01176
EP-A-0,270,356.

It will be appreciated that the instant specification is set forth by way of illustration and not limitation, and that various modifications and changes may be made without departing from the spirit and scope of the present invention.

What is claimed is:

1. A method for transforming a plant to confer on the transformed plant an increased resistance to a fungus, wherein said plant is other than a solanaceous plant, said method comprising introducing into the genome of the plant one or more lysozyme gene structures and then assaying the plant for increased resistance to said fungus, said lysozyme gene structures expressing lysozyme, said lysozyme gene structures comprising a chimeric gene fusion of the TR promoter, the signal peptide-encoding sequence of barley alpha-amylase and one or more lysozyme genes, and said transformed plant, as a result of being transformed with said lysozyme gene structures, exhibiting an increased resistance to said fungus as compared to a plant of the same species which is not so transformed.

2. The method of claim 1 wherein the lysozyme gene is of non-plant origin.

3. The method of claim 1 wherein the lysozyme gene is selected from a chicken albumen lysozyme gene, a T4-phage lysozyme gene and combinations thereof.

4. The method of claim 1 wherein the lysozyme gene structure a) is contained on plasmid pSR 2–4 or b) is a DNA sequence which acts essentially in the same manner as the lysozyme gene contained on plasmid pSR 2–4.

5. Transformed plant cells, said transformed plant cells being of a plant other than a solanaceous plant, said transformed plant cells comprising in their genome one or more lysozyme gene structures, said lysozyme gene structures expressing lysozyme, said lysozyme gene structures comprising a chimeric gene fusion of the TR promoter, the signal peptide-encoding sequence of barley alpha-amylase and one or more lysozyme genes, and said transformed plant cells, as a result of being transformed with said lysozyme gene structures, exhibiting an increased resistance to said fungus as compared to a plant cell of the same plant species and cell type which is not so transformed.

6. Transformed plant cells according to claim 5 which are protoplasts.

7. Transformed plant cells according to claim 5 wherein the lysozyme gene is of non-plant origin.

8. Transformed plant cells according to claim 5 wherein the lysozyme gene is selected from a chicken albumen lysozyme gene, a T4-phage lysozyme gene and combinations thereof.

9. Transformed plant cells according to claim 5 wherein the lysozyme gene structure a) is contained on plasmid pSR 2–4 or b) is a DNA sequence which acts essentially in the same manner as the lysozyme gene contained on plasmid pSR 2–4.

10. Transformed whole plants, said transformed whole plants being other than solanaceous plants, said transformed whole plants comprising in their genome one or more lysozyme gene structures, said lysozyme gene structures expressing lysozyme, said lysozyme gene structures comprising a chimeric gene fusion of the TR promoter, the signal peptide-encoding sequence of barley alpha-amylase and one or more lysozyme genes, and said transformed plants, as a result of being transformed with said lysozyme gene structures, exhibiting an increased resistance to said fungus as compared to a plant of the same plant species which is not so transformed.

11. Transformed whole plants according to claim 10 wherein the lysozyme gene is of non-plant origin.

12. Transformed whole plants according to claim 10 wherein the lysozyme gene is selected from a chicken albumen lysozyme gene, a T4-phage lysozyme gene and combinations thereof.

13. Transformed whole plants according to claim 10 wherein the lysozyme gene structure a) is contained on plasmid pSR 2–4 or b) is a DNA sequence which acts essentially in the same manner as the lysozyme gene contained on plasmid pSR 2–4.

14. Transformed plant parts, said transformed plant parts being of a plant other than a solanaceous plant, said transformed plant parts comprising in their genome one or more lysozyme gene structures, said lysozyme gene structures expressing lysozyme, said lysozyme gene structures comprising a chimetic gene fusion of the TR promoter, the signal peptide-encoding sequence of barley alpha-amylase and one or more lysozyme genes, and said transformed plant part, as a result of being transformed with said lysozyme gene structures, exhibiting an increased resistance to said fungus as compared to a plant part of the same plant species and part type which is not so transformed.

15. Transformed plant parts according to claim 14 which are seeds.

16. Transformed plant parts according to claim 14 wherein the lysozyme gene is of non-plant origin.

17. Transformed plant parts according to claim 14 wherein the lysozyme gene is selected from a chicken albumen lysozyme gene, a T4-phage lysozyme gene and combinations thereof.

18. Transformed plant parts according to claim 14 wherein the lysozyme gene structure a) is contained on plasmid pSR 2–4 or b) is a DNA sequence which acts essentially in the same manner as the lysozyme gene contained on plasmid pSR 2–4.

19. A method for transforming a plant cell to confer on said plant cell an increased resistance to a fungus, said transformed plant cell being of a plant other than a solanaceous plant, said method comprising introducing into the genome of said transformed plant cells one or more lysozyme gene structures, said lysozyme gene structures expressing lysozyme, said lysozyme gene structures comprising a chimetic gene fusion of the TR promoter, the signal peptide-encoding sequence of barley alpha-amylase and one or more lysozyme genes, and said transformed plant cell, as a result of being transformed with said lysozyme gene structures, exhibiting an increased resistance to said fungus as compared to a plant cell of the same plant species and cell type which is not so transformed.

20. The method according to claim 19 further comprising regenerating complete transformed plants from the transformed plant cells.

21. The method according to claim 19 further comprising making cuttings of the transformed plants or progeny of the transformed plants to obtain transformed plant parts.

22. The method according to claim 19 wherein the lysozyme gene-is of non-plant origin.

23. The method according to claim 19 wherein the lysozyme gene is selected from a chicken albumen lysozyme gene, a T4-phage lysozyme gene and combinations thereof.

24. The method according to claim 19 wherein the lysozyme gene structure a) is contained on plasmid pSR 2–4 or b) is a DNA sequence which acts essentially in the same manner as the lysozyme gene contained on plasmid pSR 2–4.

25. Plant propagation material having an increased resistance to fungi where such propagation material is obtained by multiplying transformed plant cells according to claim 5.

26. Plant propagation material having an increased resistance to fungi where such propagation material is obtained by multiplying transformed whole plants according to claim 10.

27. Plant propagation material having an increased resistance to fungi where such propagation material is obtained by multiplying transformed plant parts according to claim 14.

28. The method of claim 1 where the plant is a member of the class Dicotyledoneae.

29. The method of claim 1 where the plant is a member of the class Monocotyledoneae.

30. Transformed plant cells according to claim 5 of the class Dicotyledoneae.

31. Transformed plant cells according to claim 5 of the class Monocotyledoneae.

32. Transformed whole plants according to claim 10 of the class Dicotyledoneae.

33. Transformed whole plants according to claim 10 of the class Monocotyledoneae.

34. Transformed plant parts according to claim 14 of the class Dicotyledoneae.

35. Transformed plant parts according to claim 14 of the class Monocotyledoneae.

36. Plant propagation material according to claim 25 of the class Dicotyledoneae.

37. Plant propagation material according to claim 25 of the class Monocotyledoneae.

38. Plant propagation material according to claim 26 of the class Dicotyledoneae.

39. Plant propagation material according to claim 26 of the class Monocotyledoneae.

40. Plant propagation material according to claim 27 of the class Dicotyledoneae.

41. Plant propagation material according to claim 27 of the class Monocotyledoneae.

* * * * *

UNITED STATES PATENT AND TRADEMARK OFFICE
CERTIFICATE OF CORRECTION

PATENT NO. : 5,589,626
DATED : December 31, 1996
INVENTOR(S) : Hain, et al.

It is certified that error appears in the above-indentified patent and that said Letters Patent is hereby corrected as shown below:

Col. 15, line 57    Delete " chimetic" and substitute -- chimeric --

Col. 16, line 13    Delete " chimetic " and substitute -- chimeric --

Col. 16, line 40    Delete " chimetic " and substitute -- chimeric --

Signed and Sealed this

Fifth Day of August, 1997

Attest:

Attesting Officer

BRUCE LEHMAN

Commissioner of Patents and Trademarks